United States Patent
Hess et al.

(10) Patent No.: US 9,474,555 B2
(45) Date of Patent: Oct. 25, 2016

(54) INTERSPINOUS PROCESS IMPLANT HAVING PIN DRIVEN ENGAGEMENT ARMS

(71) Applicant: Spinal Simplicity LLC, Overland Park, KS (US)

(72) Inventors: Harold Hess, Leawood, KS (US); Todd Moseley, Olathe, KS (US); Melissa Frock, Larwill, IN (US); Adam Rogers, Norfolk, VA (US)

(73) Assignee: Spinal Simplicity LLC, Lenexa, KS (US)

( * ) Notice: Subject to any disclaimer, the term of this patent is extended or adjusted under 35 U.S.C. 154(b) by 0 days.

(21) Appl. No.: 14/303,662

(22) Filed: Jun. 13, 2014

(65) Prior Publication Data

US 2014/0371795 A1 Dec. 18, 2014

Related U.S. Application Data

(60) Provisional application No. 61/834,964, filed on Jun. 14, 2013.

(51) Int. Cl.
*A61B 17/70* (2006.01)

(52) U.S. Cl.
CPC ................. *A61B 17/7065* (2013.01)

(58) Field of Classification Search
CPC .......... A61B 17/7062; A61B 17/7065; A61B 17/7068
USPC ..................... 606/246–249; 623/17.11–17.16
See application file for complete search history.

(56) References Cited

U.S. PATENT DOCUMENTS

| | | | |
|---|---|---|---|
| 5,849,004 A * | 12/1998 | Bramlet | A61B 17/0401 606/232 |
| 8,157,842 B2 | 4/2012 | Phan et al. | |
| 8,641,762 B2 * | 2/2014 | Mitchell | A61B 17/7065 606/246 |
| 2006/0064165 A1 | 3/2006 | Zucherman et al. | |
| 2007/0161992 A1 | 7/2007 | Kwak et al. | |
| 2008/0287997 A1 * | 11/2008 | Altarac | A61B 17/7065 606/249 |
| 2009/0292316 A1 * | 11/2009 | Hess | 606/249 |
| 2011/0172710 A1 | 7/2011 | Thommen et al. | |
| 2012/0150229 A1 | 6/2012 | Hess | |

OTHER PUBLICATIONS

International Preliminary Report on Patentability for PCT/US2014/042233, dated Dec. 15, 2015.

\* cited by examiner

*Primary Examiner* — Ellen C Hammond
*Assistant Examiner* — Christina Negrellirodrigue
(74) *Attorney, Agent, or Firm* — Locke Lord LLP; Scott D. Wofsy; Arpita G. Buesing

(57) ABSTRACT

An interspinous process implant comprising an elongated body defining a longitudinal axis and an interior cavity. The implant includes engagement members movable between a first position stowed within the interior cavity and a second position deployed from the interior cavity. Each engagement member includes a central hub defining a hub axis perpendicular to the longitudinal axis of the body. Each central hub has an inwardly extending crank pin. The crank pins are radially offset from the hub axis and circumferentially spaced apart from one another. The implant also include an elongated drive shaft mounted for axial movement within the interior cavity and includes a distal actuation portion having upper and lower yokes positioned to cooperate with the crank pins. Upon axial movement of the drive shaft the crank pins translate through respective arcuate paths about the hub axis, causing corresponding rotational movement of the engagement members about the hub axis.

20 Claims, 5 Drawing Sheets

INTERSPINOUS PROCESS IMPLANT HAVING PIN DRIVEN ENGAGEMENT ARMS

CROSS-REFERENCE TO RELATED APPLICATIONS

This application claims the benefit of and priority to U.S. Provisional Patent Application No. 61/834,964 filed Jun. 14, 2013, which is incorporated by reference herein in its entirety.

BACKGROUND OF THE INVENTION

1. Field of the Invention

The subject invention is directed to surgical implants, and more particularly, to a percutaneous interspinous process implant and fusion device.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, which is surrounded by a bony channel called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness and/or a loss of balance. These symptoms often increase after walking or standing for a period of time.

There are number of non-surgical treatments of stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord or nerves between the spinous processes that protrude from the vertebrae in the lower back. A well-known implant used for performing IPD surgery is the X-STOP® device, which was first introduced by St. Francis Medical Technologies, Inc. of Alameda Calif. However, implantation of the X-STOP® device still requires an incision to access the spinal column to deploy the X-STOP® device. It would be advantageous to provide an implant for performing IPD procedures that could be percutaneously inserted into the interspinous process space and effectively treat lumbar spinal stenosis.

SUMMARY OF THE INVENTION

The subject invention is directed to a new and useful interspinous process implant for treating lumbar spinal stenosis.

The spinal implant includes, in one aspect, an elongated body dimensioned and configured for percutaneous interspinous process implantation, defining a longitudinal axis, an interior cavity and opposed proximal and distal end portions. A pair of laterally opposed engagement members are mounted for movement between a first position stowed within the interior cavity of the body and a second position deployed from the interior cavity of the body to engage the spinous process. Each engagement member includes a central hub defining a common hub axis extending perpendicular to the longitudinal axis of the body and having an inwardly extending crank pin. The inwardly extending crank pins of the two central hubs are radially offset from the hub axis and circumferentially spaced apart from one another about the hub axis.

An elongated drive shaft is mounted for axial movement within the interior cavity of the body along the longitudinal axis thereof and includes a distal actuation portion having upper and lower yokes positioned to cooperate circumferentially with the crank pins. Axial movement of the drive shaft causes the two crank pins to translate through respective arcuate paths about the hub axis, causing corresponding rotational movement of the laterally opposed engagement members about the hub axis.

Each engagement member includes a pair of diametrically opposed arms extending radially outwardly from the central hub thereof. Each arm has a inner curved portion and an outer claw portion. Preferably, the engagement members are mounted for rotation about a common axle extending along the hub axis.

In one aspect of the present invention a means for axially moving the drive shaft along the longitudinal axis of the body within the interior cavity thereof is disclosed. The means for axially moving the drive shaft includes a rotatable cap operatively associated with the proximal end portion of the body and having a threaded bore configured to receive a threaded shaft portion of the drive shaft. Rotation of the cap causes corresponding axial movement of the drive shaft within the interior cavity of the body.

In another aspect of the invention a means for axially moving the drive shaft includes a ratchet assembly operatively associated with the proximal end portion of the body and having an axially advanceable rack engaged with a proximal end of the drive shaft. A pawl ring is retained within the interior cavity, whereby axial advancement of rack relative to the pawl ring causes corresponding axial movement of the drive shaft within the interior cavity of the body.

In yet another aspect of the invention a nose cone assembly is mounted at the distal end portion of the body to provide structural rigidity to the body implant. These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the flexible diaphragm coupling element of the subject invention without undue experimentation, preferred embodiments thereof will be described in detail hereinbelow with reference to certain figures, wherein.

DETAILED DESCRIPTION OF PREFERRED EMBODIMENTS

Figure 1:
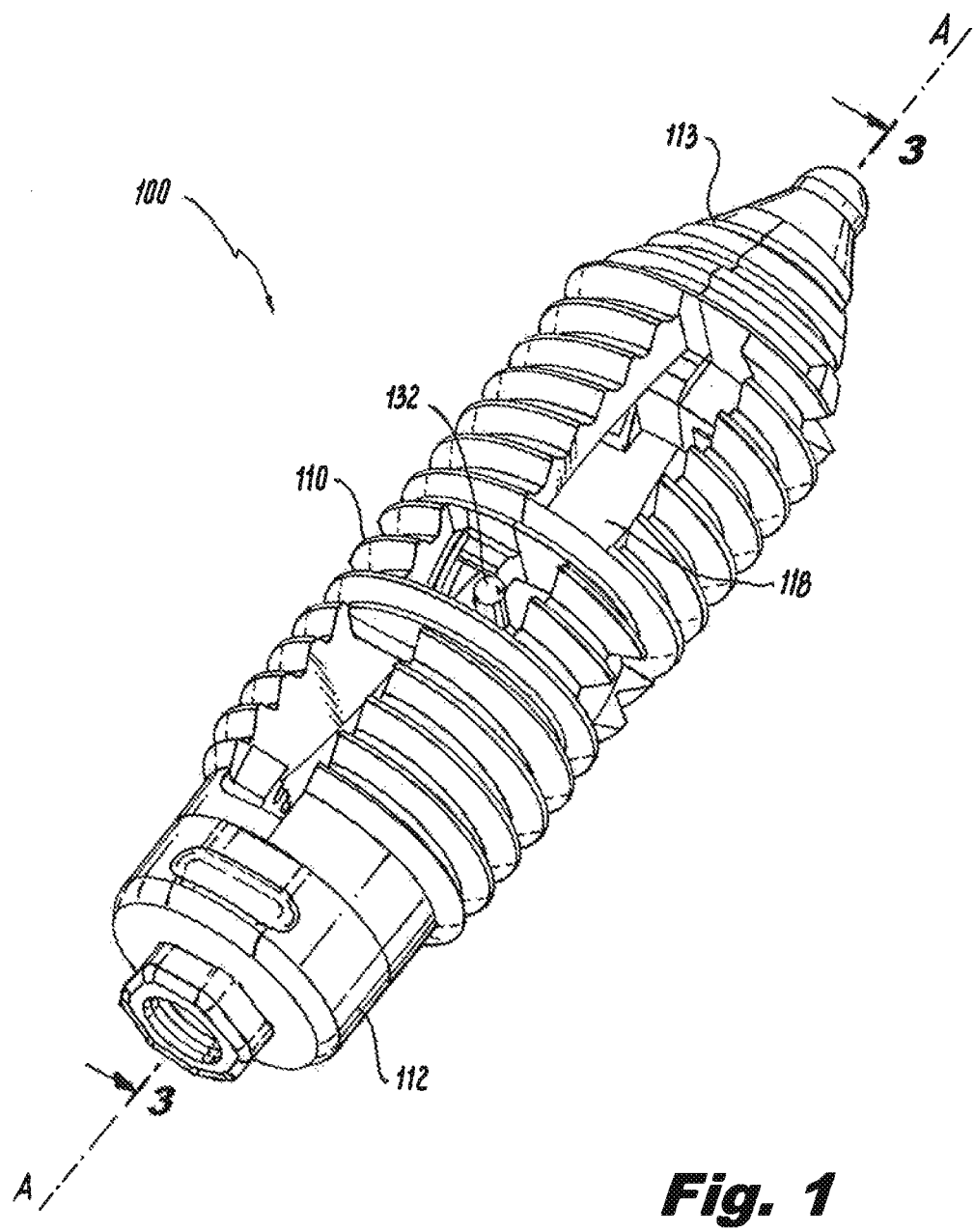
FIG. 1 is a perspective view of an interspinous implant in accordance the present invention illustrating a threaded body having engagement arms in a stowed position within an interior cavity of the threaded body.

Referring to FIG. 1, there is illustrated an embodiment of an interspinous implant constructed in accordance with the present invention and designated generally by reference numeral 100. Implant is particularly well adapted for use in performing minimally invasive surgical procedures for treating spinal stenosis, including, for example, interspinous process decompression (IPD).

Figure 3:
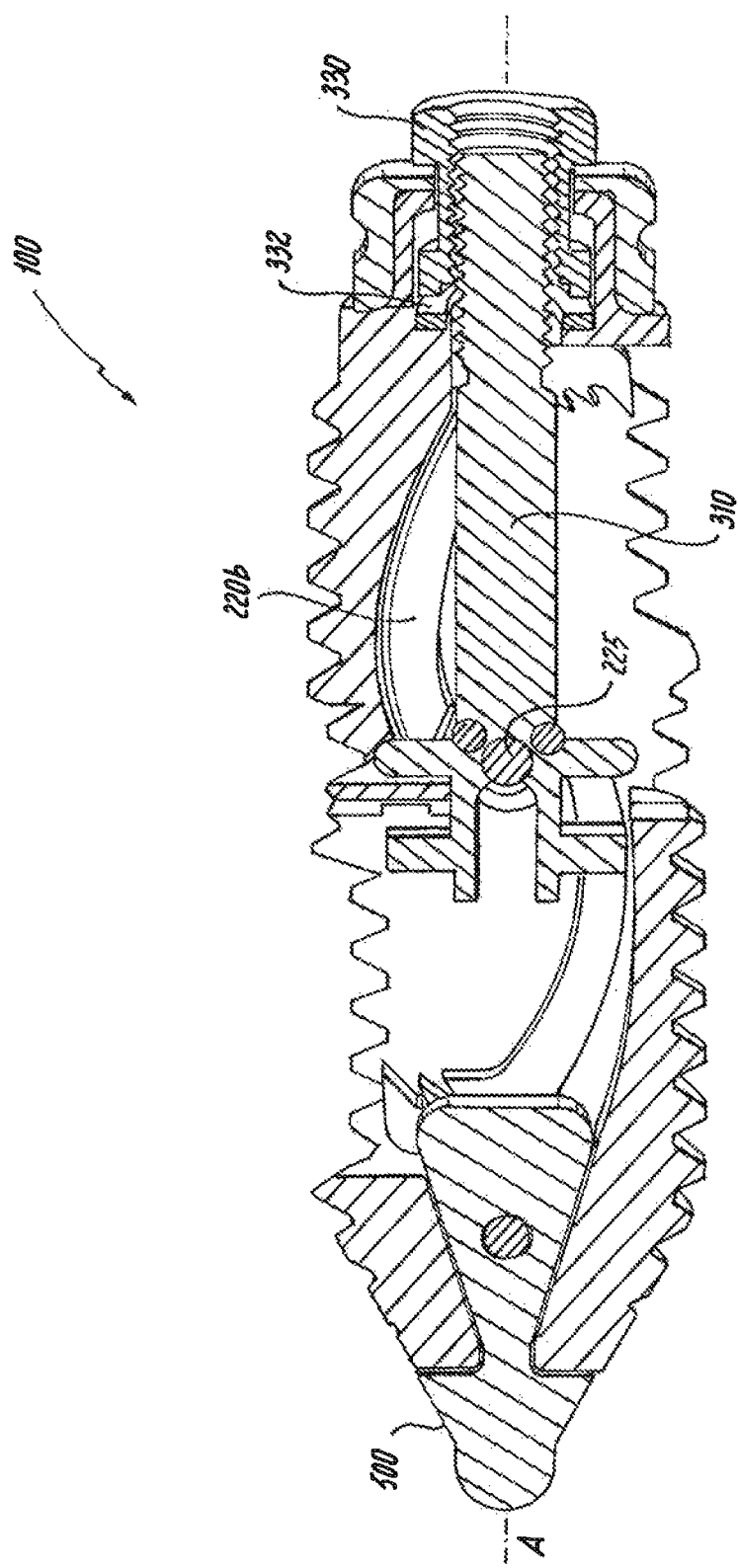
FIG. 3 is a cross-section view of the implant of FIG. 1 taken along line 3-3 of FIG. 1.

As shown in FIG. 1, interspinous implant 100 includes an elongated threaded body 110 configured for percutaneous interspinous process implantation defining a longitudinal axis "A" and having opposed proximal 112 and distal portions 113. The body 110 has a right body section 110a and a left body section 110b (shown in FIG. 3). The body sections 110a, 110b are held together in part by a spindle shaft 132 and retaining ring 134 located at a central portion of the implant 100 and a securement shaft 114 and retaining ring 116 located proximate a nose assembly 500. In addition, a locking cap 160 is operatively associated with the proximal portion 112. The locking cap 160 supports the spindle shaft 132 and the securement shaft 114 in holding the right and left body sections 110a, 110b together. Additional detail regarding the material and dimensions of the body sections 110a, 110b are described in U.S. Pat. No. 8,142,479 and U.S. Patent Publication No. 2012/0150229, both of which are incorporated herein by reference in their entirety.

Figure 2:
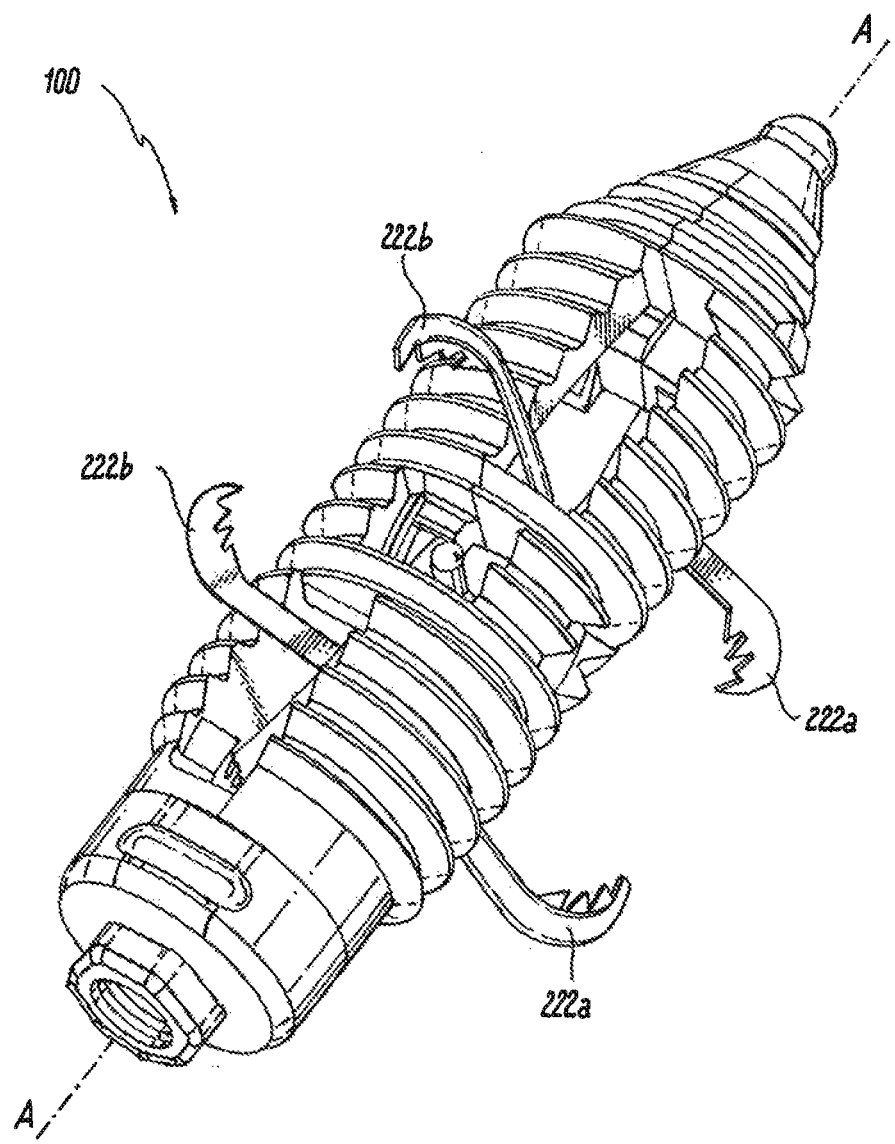
FIG. 2 is a perspective view of the implant of FIG. 1 with the engagement arms disposed in a deployed position extending from the interior cavity of the threaded body portion.

The body 110 of the implant 110 defines an interior cavity 118 or chamber which houses two laterally opposed engagement members 220a, 220b formed from titanium, stainless steel, ceramic, composite, or a similar high-strength, lightweight biocompatible metal. The engagement members 220a, 220b are mounted for movement between a first position (shown in FIG. 1) stowed within the interior cavity 118 of the body 110 and a second position (shown in FIG. 2) deployed from the interior cavity 118 of the body 110 to engage the spinous process. Once the engagement members 220a, 220b are deployed to engage the spinous process, migration of the implant 100 is inhibited, in addition to lateral migration resistance provided by the threads alone.

Figure 4:
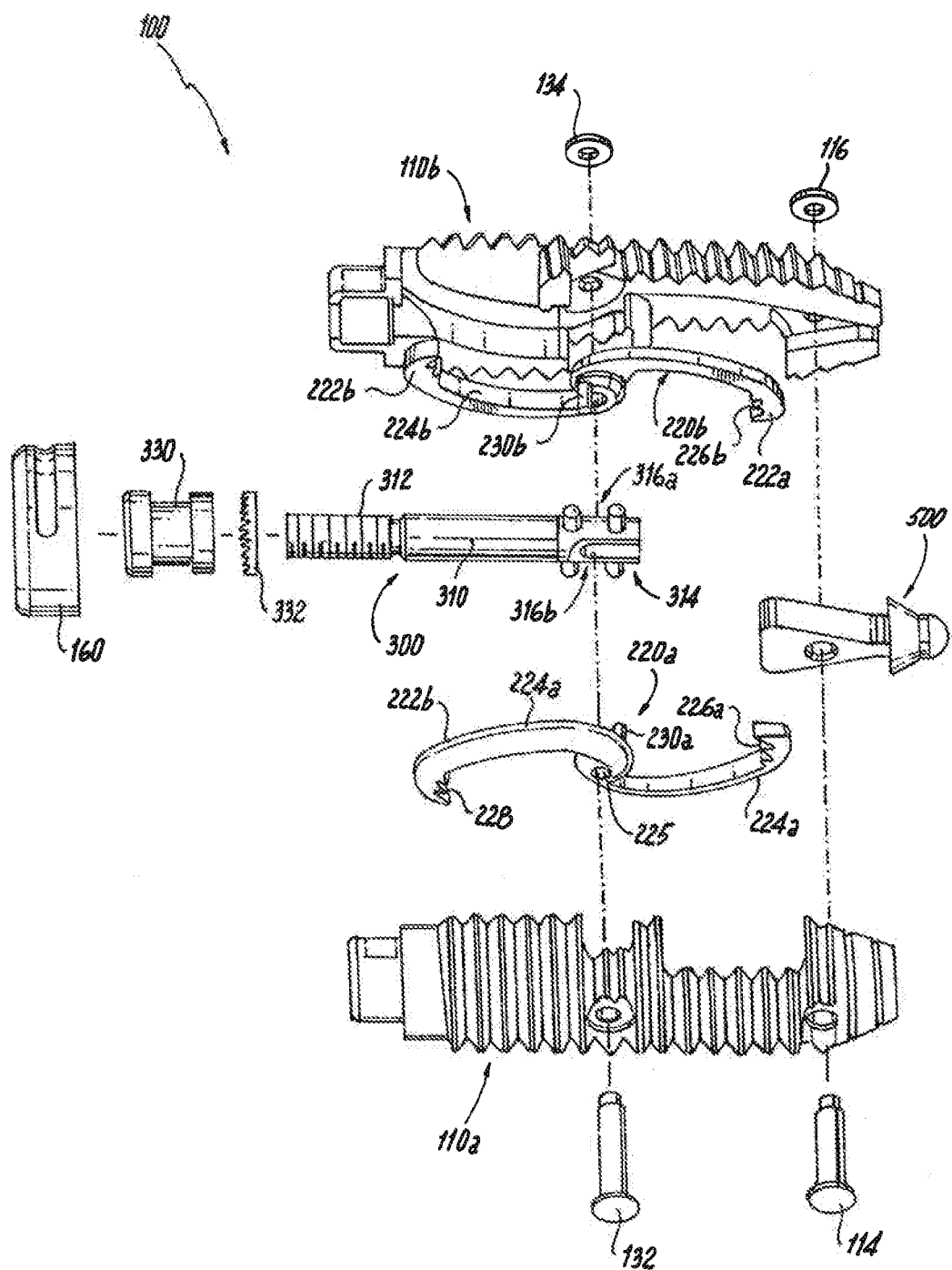
FIG. 4 is an exploded perspective view of the implant of FIG. 1, with parts separated.

As shown in FIG. 4, each engagement member 220a, 220b includes a pair of diametrically opposed arms 222a, 222b extending radially outwardly from a central hub 225. Each arm 222a, 222b, includes an inner curved portion 224a, 224b and outer claw portion 226a, 226b. The outer claw portions 226a, 226b are preferably each provided with a plurality of sharpened teeth 228 for engaging and puncturing the bone of the adjacent spinous processes, to effect stabilization of the implant 100. The teeth 228 on each claw portion 226a, 226b are preferably dissimilar in size and orientation, to better engage an individual's particular spinal anatomy, which may vary between patients in both size and shape.

The central hub 225 of each engagement member 220a, 220b defines a common hub axis extending perpendicular to a longitudinal axis of the body 112. The spindle shaft 132 securing the right and left body portions 110a, 110b is secured in place through an aperture of the central hub 225. Each central hub 225 has an inwardly extending crank pin 230a, 230b. The crank pins 230a, 230b are preferably radially offset from the hub axis and circumferentially spaced apart from one another about the hub axis.

The implant 100 further includes an actuation assembly 300 having an elongated drive shaft 310 mounted for axial movement within the interior cavity 118 of the body 112 along the longitudinal axis thereof. The drive shaft 310 includes a proximal threaded portion 312 and a distal actuation portion 314. The distal actuation portion 314 has upper and lower yokes 316a, 316b positioned to cooperate with the crank pins 230a, 230b of the central hubs 224. Both the upper and lower yokes 316a, 316b resemble U-shaped pieces that extend outwardly from the drive shaft 310. As known in the art, the U-shaped pieces of the yoke aid in holding and controlling the movement of mechanical parts, in this instance the crank pins 230a, 230b. Upon axial movement of the drive shaft 300, the two crank pins 230a, 230b translate through respective arcuate paths about the hub axis causing corresponding rotational movement of the engagement members 220a, 220b about the hub axis.

In one embodiment, shown in FIG. 4, the means for axially moving the drive shaft 310 is defined by a rotatable cap 330 operatively associated with the proximal threaded portion 312 of the drive shaft 310. The rotatable cap 330 includes a threaded bore 332 configured to receive the proximal threaded portion 312. In this embodiment, once the implant 100 is positioned as desired between adjacent vertebral processes, the cap 330 is rotated to effect axial movement of the drive shaft 310 into the interior cavity 118 and deploy the engagement arms 222a, 222b into the second position. Similarly, rotating the cap 330 in an opposing direction, effects axial movement in the reverse direction. Thereby returning the engagement arms 222a, 222b, to the first position and permitting removal of the implant 100. The threaded bore 332 includes beveled teeth to engage the proximal threaded portion 312 and maintain friction between the rotatable cap 330 and the proximal threaded portion 312 to secure the cap 300 as the cap 330 rotates.

Figure 5:
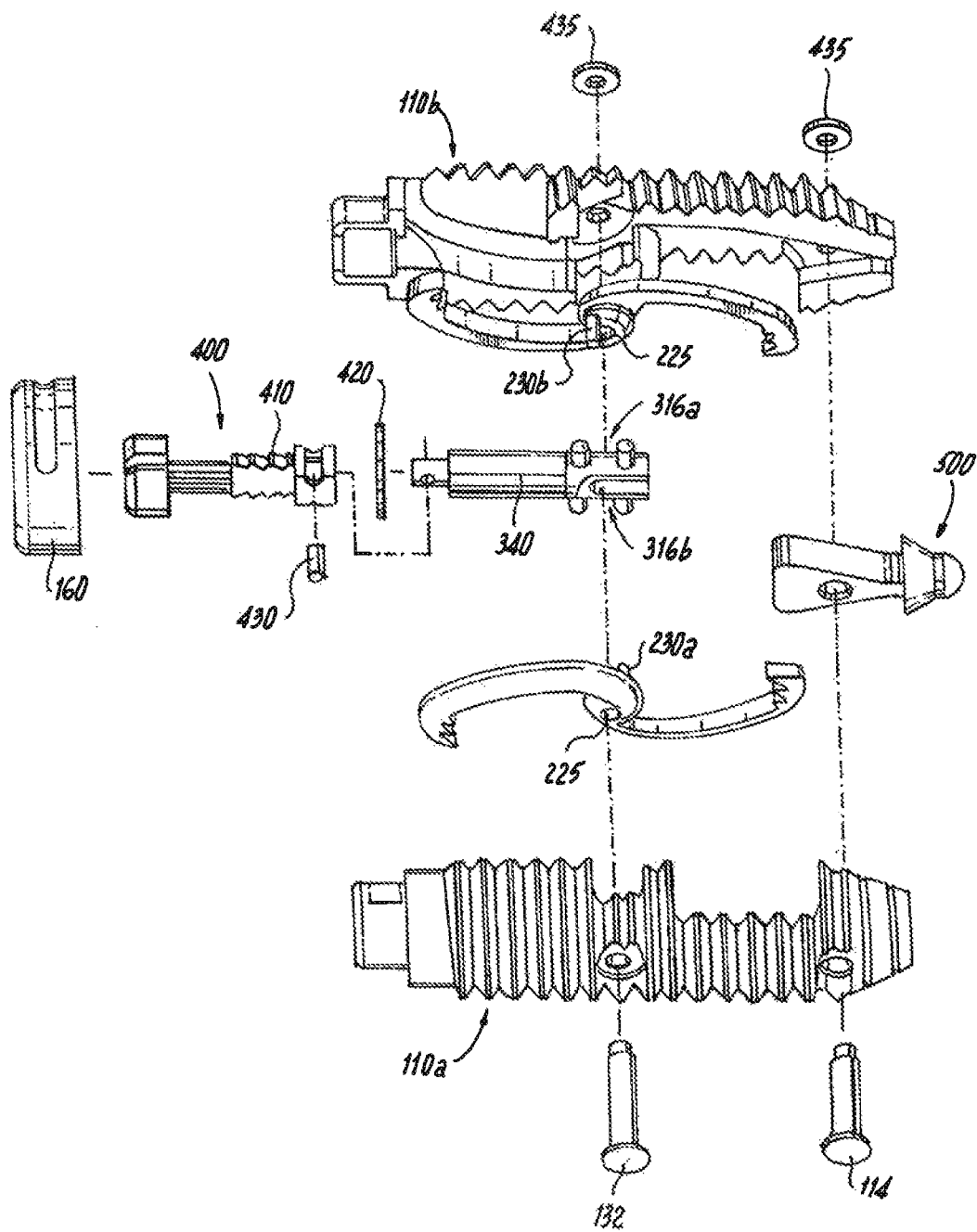
FIG. 5 is an exploded perspective view of a further embodiment an implant in accordance with the present invention.

In an alternate embodiment, shown in FIG. 5, a ratchet assembly 400 is utilized as a means for axially moving the drive shaft. The ratchet assembly 400 includes an advanceable rack 410 operatively associated with a proximal end 340 of the drive shaft 310. A pawl ring 420 is retained within the interior cavity 118. A drive pin 430 is associated with the proximal end 340 of the drive shaft 310 to secure the drive shaft 310 and ratchet assembly 400. In this embodiment, axial advancement of the rack 410 relative to the pawl ring 420 causes corresponding axial movement of the drive shaft 310 within the interior cavity 118 of the body 110. As shown in FIG. 5, a plurality of washers 435, known in the art, may be disposed between the spindle shaft 132 and the central hub 225 and the securement shaft 114 and the nose assembly 500 to prevent friction and maintain pressure when the left and right body sections 110a, 110b are secured together.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. An interspinous process implant, comprising:
   a) an elongated body dimensioned and configured for percutaneous interspinous process implantation, defining a longitudinal axis, an interior cavity and opposed proximal and distal end portions;
   b) a pair of laterally opposed engagement members mounted for movement between a first position stowed within the interior cavity of the body and a second position deployed from the interior cavity of the body to engage the spinous process, each engagement member including a central hub defining a common hub axis extending perpendicular to the longitudinal axis of the body and having an inwardly extending crank pin, wherein the inwardly extending crank pins of the two central hubs are radially offset from the hub axis and circumferentially spaced apart from one another about the hub axis, and wherein each engagement member includes a pair of diametrically opposed arms extending radially outwardly from the central hub thereof, each arm having an inner curved portion and an outer claw portion; and
   c) an elongated drive shaft mounted for axial movement within the interior cavity of the body along the longitudinal axis thereof and including a distal actuation portion having upper and lower yokes positioned to cooperate with the circumferentially spaced apart inwardly extending crank pins of the two central hubs of the engagement members, whereby axial movement of the drive shaft causes the two crank pins to translate through respective arcuate paths about the hub axis, causing corresponding rotational movement of the laterally opposed engagement members about the hub axis.

2. An interspinous process implant as recited in claim 1, wherein the engagement members are mounted for rotation about a common axle extending along the hub axis.

3. An interspinous process implant as recited in claim 1, further comprising means for axially moving the drive shaft along the longitudinal axis of the body within the interior cavity thereof.

4. An interspinous process implant as recited in claim 3, wherein the means for axially moving the drive shaft includes a rotatable cap operatively associated with the proximal end portion of the body and having a threaded bore configured to receive a threaded shaft portion of the drive shaft, whereby rotation of the cap causes corresponding axial movement of the drive shaft within the interior cavity of the body.

5. An interspinous process implant as recited in claim 3, wherein the means for axially moving the drive shaft includes a ratchet assembly operatively associated with the proximal end portion of the body and having an axially advanceable rack engaged with a proximal end of the drive shaft and a pawl ring retained within the interior cavity, whereby axial advancement of rack relative to the pawl ring causes corresponding axial movement of the drive shaft within the interior cavity of the body.

6. An interspinous process implant as recited in claim 1, further comprising a nose cone assembly mounted at the distal end portion of the body to provide structural rigidity to the body implant.

7. An interspinous process implant, comprising:
   a) an elongated body dimensioned and configured for percutaneous interspinous process implantation, defining a longitudinal axis, an interior cavity and opposed proximal and distal end portions;
   b) a pair of laterally opposed engagement members mounted for movement between a first position stowed within the interior cavity of the body and a second position deployed from the interior cavity of the body to engage the spinous process, each engagement member including a central hub defining a common hub axis extending perpendicular to the longitudinal axis of the body and having an inwardly extending crank pin, wherein the inwardly extending crank pins of the two central hubs are radially offset from the hub axis and circumferentially spaced apart from one another about the hub axis, and wherein the engagement members are mounted for rotation about a common axle extending along the hub axis; and
   c) an elongated drive shaft mounted for axial movement within the interior cavity of the body along the longitudinal axis thereof and including a distal actuation portion having upper and lower yokes positioned to cooperate with the circumferentially spaced apart inwardly extending crank pins of the two central hubs of the engagement members, whereby axial movement of the drive shaft causes the two crank pins to translate through respective arcuate paths about the hub axis, causing corresponding rotational movement of the laterally opposed engagement members about the hub axis.

8. An interspinous process implant as recited in claim 7, wherein each engagement member includes a pair of diametrically opposed arms extending radially outwardly from the central hub thereof, each arm having an inner curved portion and an outer claw portion.

9. An interspinous process implant as recited in claim 7, further comprising means for axially moving the drive shaft along the longitudinal axis of the body within the interior cavity thereof.

10. An interspinous process implant as recited in claim 9, wherein the means for axially moving the drive shaft includes a rotatable cap operatively associated with the proximal end portion of the body and having a threaded bore configured to receive a threaded shaft portion of the drive shaft, whereby rotation of the cap causes corresponding axial movement of the drive shaft within the interior cavity of the body.

11. An interspinous process implant as recited in claim 9, wherein the means for axially moving the drive shaft includes a ratchet assembly operatively associated with the proximal end portion of the body and having an axially advanceable rack engaged with a proximal end of the drive shaft and a pawl ring retained within the interior cavity, whereby axial advancement of rack relative to the pawl ring causes corresponding axial movement of the drive shaft within the interior cavity of the body.

12. An interspinous process implant as recited in claim 7, further comprising a nose cone assembly mounted at the distal end portion of the body to provide structural rigidity to the body implant.

13. An interspinous process implant, comprising:
   a) an elongated body dimensioned and configured for percutaneous interspinous process implantation, defining a longitudinal axis, an interior cavity and opposed proximal and distal end portions;

b) a pair of laterally opposed engagement members mounted for movement between a first position stowed within the interior cavity of the body and a second position deployed from the interior cavity of the body to engage the spinous process, each engagement member including a central hub defining a common hub axis extending perpendicular to the longitudinal axis of the body and having an inwardly extending crank pin, wherein the inwardly extending crank pins of the two central hubs are radially offset from the hub axis and circumferentially spaced apart from one another about the hub axis;

c) an elongated drive shaft mounted for axial movement within the interior cavity of the body along the longitudinal axis thereof and including a distal actuation portion having upper and lower yokes positioned to cooperate with the circumferentially spaced apart inwardly extending crank pins of the two central hubs of the engagement members, whereby axial movement of the drive shaft causes the two crank pins to translate through respective arcuate paths about the hub axis, causing corresponding rotational movement of the laterally opposed engagement members about the hub axis; and d) a rotatable cap operatively associated with the proximal end portion of the body and having a threaded bore configured to receive a threaded shaft portion of the drive shaft, whereby rotation of the cap causes corresponding axial movement of the drive shaft within the interior cavity of the body.

14. An interspinous process implant as recited in claim 13, wherein each engagement member includes a pair of diametrically opposed arms extending radially outwardly from the central hub thereof, each arm having an inner curved portion and an outer claw portion.

15. An interspinous process implant as recited in claim 14, wherein the engagement members are mounted for rotation about a common axle extending along the hub axis.

16. An interspinous process implant as recited in claim 14, further comprising a nose cone assembly mounted at the distal end portion of the body to provide structural rigidity to the body implant.

17. An interspinous process implant, comprising:
a) an elongated body dimensioned and configured for percutaneous interspinous process implantation, defining a longitudinal axis, an interior cavity and opposed proximal and distal end portions;

b) a pair of laterally opposed engagement members mounted for movement between a first position stowed within the interior cavity of the body and a second position deployed from the interior cavity of the body to engage the spinous process, each engagement member including a central hub defining a common hub axis extending perpendicular to the longitudinal axis of the body and having an inwardly extending crank pin, wherein the inwardly extending crank pins of the two central hubs are radially offset from the hub axis and circumferentially spaced apart from one another about the hub axis;

c) an elongated drive shaft mounted for axial movement within the interior cavity of the body along the longitudinal axis thereof and including a distal actuation portion having upper and lower yokes positioned to cooperate with the circumferentially spaced apart inwardly extending crank pins of the two central hubs of the engagement members, whereby axial movement of the drive shaft causes the two crank pins to translate through respective arcuate paths about the hub axis, causing corresponding rotational movement of the laterally opposed engagement members about the hub axis; and d) a ratchet assembly operatively associated with the proximal end portion of the body and having an axially advanceable rack engaged with a proximal end of the drive shaft and a pawl ring retained within the interior cavity, whereby axial advancement of rack relative to the pawl ring causes corresponding axial movement of the drive shaft within the interior cavity of the body.

18. An interspinous process implant as recited in claim 17, wherein each engagement member includes a pair of diametrically opposed arms extending radially outwardly from the central hub thereof, each arm having an inner curved portion and an outer claw portion.

19. An interspinous process implant as recited in claim 18, wherein the engagement members are mounted for rotation about a common axle extending along the hub axis.

20. An interspinous process implant as recited in claim 18, further comprising a nose cone assembly mounted at the distal end portion of the body to provide structural rigidity to the body implant.

* * * * *